United States Patent [19]
Barlow

[11] Patent Number: 5,494,637
[45] Date of Patent: Feb. 27, 1996

[54] ENDOSCOPE WASHER

[75] Inventor: David E. Barlow, Hicksville, N.Y.

[73] Assignee: Olympus America Inc., Lake Success, N.Y.

[21] Appl. No.: 272,892

[22] Filed: Jul. 8, 1994

[30] Foreign Application Priority Data

Aug. 9, 1993 [JP] Japan ................................. 5-197307

[51] Int. Cl.$^6$ ............................... A61L 2/00; B08B 9/00
[52] U.S. Cl. ........................ 422/28; 422/106; 422/292; 422/300; 134/95.3; 134/170; 134/171
[58] Field of Search ................................. 422/1, 28, 292, 422/297, 300, 106; 134/95.3, 95.1, 166 R, 170, 171, 26

[56] References Cited

U.S. PATENT DOCUMENTS

| 4,281,674 | 8/1981 | Tanaka et al. | 134/171 |
|---|---|---|---|
| 4,763,678 | 8/1988 | Ott | 134/171 |
| 5,225,160 | 7/1993 | Sanford et al. | 422/28 |
| 5,288,467 | 2/1994 | Biermaier | 134/170 |

FOREIGN PATENT DOCUMENTS 2248188   4/1992   United Kingdom ................. 422/28

*Primary Examiner*—Robert J. Warden
*Assistant Examiner*—Theresa T. Snider
*Attorney, Agent, or Firm*—Kenyon & Kenyon

[57] ABSTRACT

Endoscope washer and washing method for providing an endoscope washer which self-disinfects the washing basin and the fluid tubes automatically, each time an endoscope is washed and disinfected. The endoscope washer includes a washing and disinfecting basin having an endoscope holding portion for holding an endoscope and a washing fluid well for storing a washing fluid. The washer also including a water supply pipe, connected to a first water supply tube and a second water supply tube, for supplying a washing fluid to the endoscope holding portion and the washing fluid well. The washer also has a disinfectant tank for supplying a disinfectant to the endoscope holding portion and the washing fluid well through the water supply pipe, to provide a self-washing function for washing and disinfecting both the endoscope and the pipes, e.g., the water supply pipes, at the same time.

19 Claims, 9 Drawing Sheets

FIG. 9

ENDOSCOPE WASHER

FIELD OF THE INVENTION

The present invention relates to endoscope washers, and more particularly to an endoscope washer for washing and disinfecting a used endoscope.

BACKGROUND OF THE INVENTION

Since an endoscope is contaminated once it is used, it must be washed and disinfected or sterilized after use, in order to avoid nosocomial infection. For this purpose, an endoscope washer is used. In accordance with known endoscope-washing procedures, an endoscope is first set in a washing basin of an endoscope washer, then a washing fluid is sprayed through a nozzle provided in the washing basin. In this manner, washing fluid is supplied through the internal lumens which are thereby cleaned by the washing fluid.

After the washing, a disinfectant fluid is sprayed in the same manner as described above or, alternatively the endoscope being cleaned is immersed in a sterilant or disinfectant fluid. In this manner the disinfectant fluid contacts the external surfaces and internal lumens of the endoscope. Thus, the endoscope is disinfected. Thereafter, washing water is sprayed over the external surface and passed through the internal lumens of the endoscope, thereby rinsing the endoscope. Finally, air is supplied through the tube of the endoscope, and the washing basin is heated, to dry both the outer surface and the inside of the endoscope tube being cleaned.

Conventional endoscope washers which are used to perform the above described cleaning procedure have the following problems. In the known endoscope washers, the tubes and fluid holding tanks tend to become colonized with bacteria, which contaminates the washer. Because of this, most washers have a special self-disinfection process which the user must periodically perform to disinfect the washer itself. However, this self-disinfection process may not decontaminate all internal portions of the washer, and may require manual steps on the part of the user. Accordingly, the conventional self-disinfection process is an inconvenience to perform.

In general, the known endoscope washers use large amounts of water for washing. If this water is unprocessed, the tap water brings organisms into the washer, which increases the need for self-disinfection. While sterilization of the water used for washing by, e.g., filtering or UV treatment, offers one way of reducing the need for self-disinfection, the expense of high processing large quantities of tap water to sterilize the water must be incurred.

SUMMARY OF THE PRESENT INVENTION

The present invention has been made in consideration of the above described problems. Accordingly, the object of the present invention is to provide an endoscope washer which self-disinfects its basins and fluid tubes automatically each time an endoscope is washed and sterilized/disinfected, not requiring special processes to be performed by the user in order to sterilize/disinfect the washer. Another object of the present invention is to use unprocessed water, e.g., tap water for washing, and processed, e.g., sterilized, water for rinsing without decreasing the performance of the endoscope, but with a decrease in operating costs as compared to endoscope washers which use only sterilized water.

In order to achieve the above object of the present invention, in one exemplary embodiment, an endoscope washer comprises a washing and disinfecting basin which includes an endoscope holding portion for holding an endoscope and a washing fluid well for storing a washing fluid. In the exemplary embodiment, the endoscope washer also includes a washing fluid tube, connected to a washing fluid supply source, for supplying a washing fluid to the endoscope holding portion and the washing fluid well, and a sterilant/disinfection fluid tank for supplying a sterilant/disinfectant fluid to the endoscope holding portion and the washing fluid well through the washing fluid tube, to provide a self-washing function for washing and sterilizing/disinfecting the endoscope and the washing fluid tube simultaneously.

Generally, the endoscope washer of the present invention may be described as having the following characteristics:

(1) The endoscope holding portion, the washing fluid well, and the washing fluid tube are washed and sterilized/disinfected simultaneously with the endoscope. Thus, there is no need for a separate washer self-sterilization/disinfection cycle.

(2) The same washing and sterilant/disinfectant fluids are used to treat both the washer and the endoscope simultaneously.

(3) The washer is designed to use tap water for high volume non-sterile washing functions and to use sterile filtered water for rinsing after sterilization/disinfection. This conserves expense in water filtering costs, and prevents tap water from permanently contaminating the washer.

BRIEF DESCRIPTION OF THE DRAWINGS

FIG. 9 is a schematic diagram illustrating another embodiment of the endoscope washer according to the present invention.

DETAILED DESCRIPTION

An embodiment of the present invention will now be described with reference to the accompanying drawings.

Figure 1:
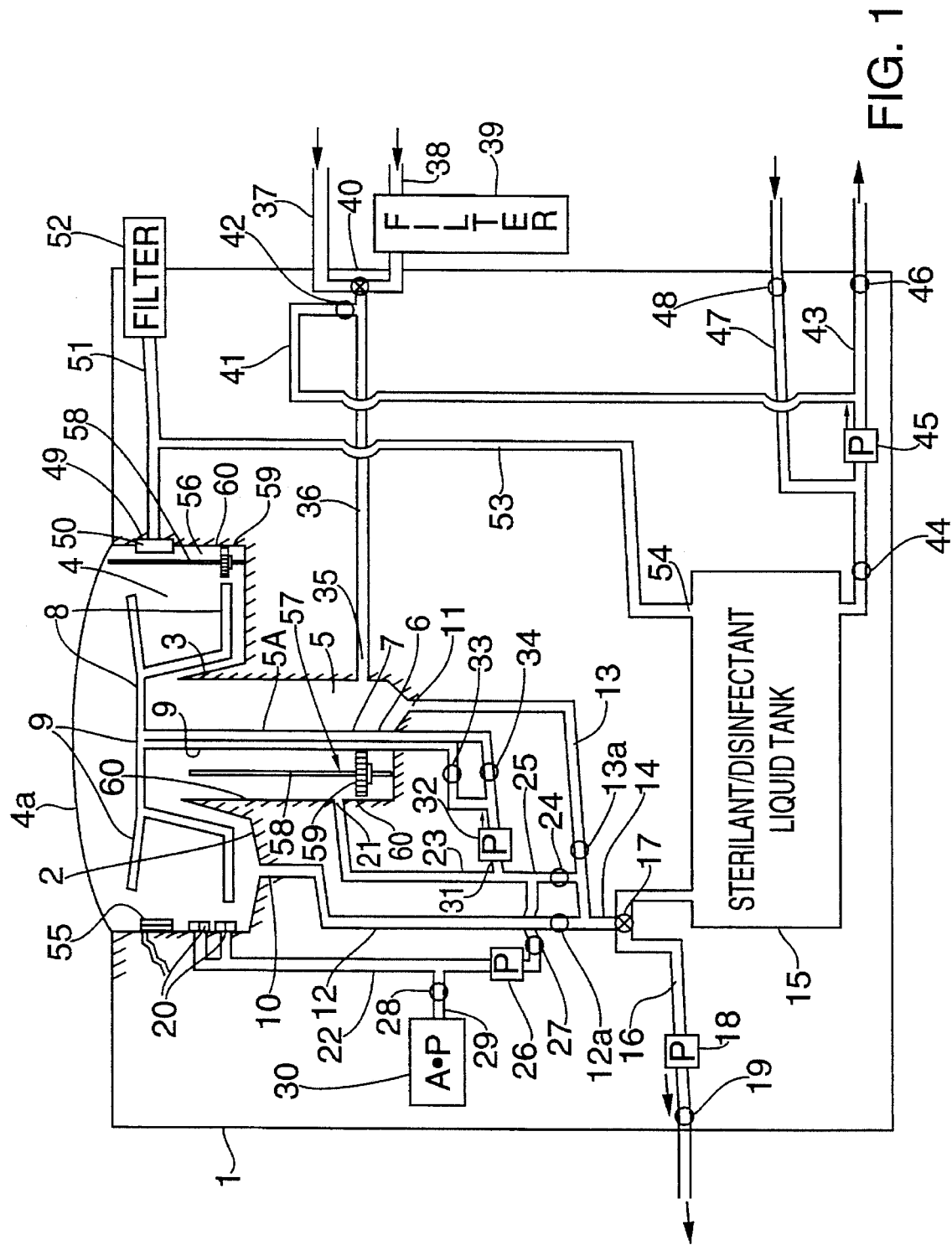
FIG. 1 is a schematic diagram illustrating an endoscope washer in accordance with one embodiment of the present invention.

FIG. 1 schematically illustrates an endoscope washer according to the present invention. A washing and disinfecting basin 2 is provided in an upper portion of a washer main body. The washing and disinfecting basin 2 is divided into two separate sections. Outside a partition 3, a doughnut-shaped endoscope holding section 4 is formed to hold an endoscope (not shown) to be washed and sterilized/disinfected. Inside the partition 3, a washing fluid well 5 for storing a washing fluid and a sterilant/disinfectant fluid is formed. A supporting member (not shown) for supporting an endoscope is formed in the endoscope holding section 4. An opening of the endoscope holding section 4 is closed by a transparent cover 4a.

In the washing and disinfecting basin 2, a central rotor 5A, which can be rotated by a motor (not shown), extends vertically through the washing fluid well 5. First and second fluid supplying pipes 6 and 7, serving as washing fluid passageways, are formed in the central rotor 5A. In an upper portion of the central rotor 5A, upper and lower fluid supplying branch pipes 8, communicating with the first and second fluid supplying pipes 6 and 7, extend in the interior of the endoscope holding section 4. A plurality of nozzles 9 are formed in portions of the first and second fluid supplying pipes 6 and 7 and the fluid supplying branch pipes 8, to spray the washing fluid or the sterilant/disinfectant fluid upward and downward to the endoscope.

A first drain port 10 is formed on a bottom portion of the endoscope holding portion 4 of the washing and disinfecting basin 2. A second drain port 11 is formed on a bottom portion of the washing fluid well 5. The first drain port 10 is connected to a first drain 12 which serves as a washing fluid passageway and has a first opening and closing valve 12a. The second drain port 11 is connected to a second drain 13 which serves as a washing fluid passageway and has a second opening and closing valve 13a.

The first and second drains 12 and 13 join together to a joining pipe 14, which branches into two pipes. One of the two pipes is connected to a sterilant/disinfectant tank 15 for storing sterilant/disinfectant, provided under the washer main body 1, while the other pipe extends outside the washer main body 1 through a discharge pipe 16. A first switching valve 17 is provided at the branch portion of the joining pipe 14. A first pump 18 and a third opening and closing valve 19 are formed in intermediate portions of the discharge pipe 16.

Provided on a side wall of the endoscope holding section 4 are connectors 20 which are to be connected to channels of an endoscope, such as air and water supplying channels (internal lumens) and forceps channels. A fluid discharge port 21 is formed in a side wall of the washing fluid well 5.

The connectors 20 are connected to an end of a first tube 22 that serves as a washing fluid passageway. The fluid discharge port 21 is connected to an end of a second tube 23 that serves as a washing fluid passageway. The other ends of the first tube 22 and the second tube 23 are connected to each other, and this connecting portion is connected to an intermediate portion of the second drain 13 via a joining pipe 25 having a fourth opening and closing valve 24. A second pump 26 and a fifth opening and closing valve 27 are formed in intermediate portions of the first tube 22. An air pump 30 is connected to an intermediate portion of the first tube 22 through a branch pipe 29 having a sixth opening and closing valve 28.

A branch pipe 31 is connected to an intermediate portion of the second tube 23, and a third pump 32 is formed in an intermediate portion of the branch pipe 31. The discharge side of the third pump 32 is connected to the first and second fluid supplying pipes 6 and 7, which have seventh and eighth opening and closing valves 33 and 34, respectively.

A fluid supplying port 35 is formed on a side wall of the washing fluid well 5. The fluid supplying port 35 is connected to an end of a water supplying pipe 36 serving as a washing fluid passageway. The other end of the water supplying pipe 36 is connected to first and second water supplying tubes 37 and 38 via a branch portion. The first water supplying tube 37 is connected to a water pipe serving as a washing fluid supplying source to supply tap water to the washer. A sterilized filter 39 of 0.22 μm mesh is provided in the second water supplying tube 38 to filter warmed water and supply sterile water to the washer.

A second switching valve 40 is formed in a branch portion between the first and second water supplying tubes 37 and 38. A third tube 41 is branched from the water supplying pipe 36. A ninth opening and closing valve 42 is formed in an intermediate portion of the third tube 41, which is connected to an intermediate portion of a fourth tube 43 connected to the sterilant/disinfectant tank 15.

In the fourth tube 43, a tenth opening and closing valve 44, a fourth pump 45, and an eleventh opening and closing valve 46 are formed in this order from the upstream side. The third tube 41 is connected to a portion between the fourth pump 45 and the eleventh opening and closing valve 46. A branch tube 47 is branched from a portion of the fourth tube 43 between the tenth opening and closing valve 44 and the fourth pump 45. A twelfth opening and closing valve 48 is formed in the branch tube 47.

The twelfth opening and closing valve 48 is opened only when a sterilant/disinfectant is supplied to the sterilant/disinfectant tank 15. The eleventh opening and closing valve 46 is opened only when the sterilant/disinfectant in the sterilant/disinfectant tank 15 is contaminated and should be exchanged.

On a side wall of the endoscope holding section, a vent 49 is formed above the surface of the fluid, and a sterile filter 50 is attached to the vent 49. One end of an air tube 51 is connected to the vent 49. The other end thereof is opened through a side wall of the washer main body 1, and a charcoal filter 52 is attached to the opening. One end of an air branch tube 53 is connected to an intermediate portion of the air tube 51 and the other end thereof is connected to an air vent 54 of the sterilant/disinfectant tank 15. A detergent box 55 is provided on a portion of the side wall of the endoscope holding section 4 at the same level as the sterile filter 50.

Fluid level sensors 56 and 57 are provided in the endoscope holding section 4 and the washing fluid well 5. Each of the level sensors 56 and 57 is constituted by a guide post 58, a permanent magnet 59 mounted on a float which is movably engaged with the guide post 58 so as to be movable up and down in accordance with the level of the fluid, and a magnetic sensor element 60 attached on the inner wall of the endoscope holding section 4 or the washing fluid well 5.

An endoscope washing and self-sterilizing/disinfecting operation by the above described endoscope washer of the present invention will now be described as a series of operation steps in the sequence the steps are performed to complete the washing and self-sterilizing/disinfecting operation.

Step Of Filling The Endoscope Washer With Tap Water

Figure 2:
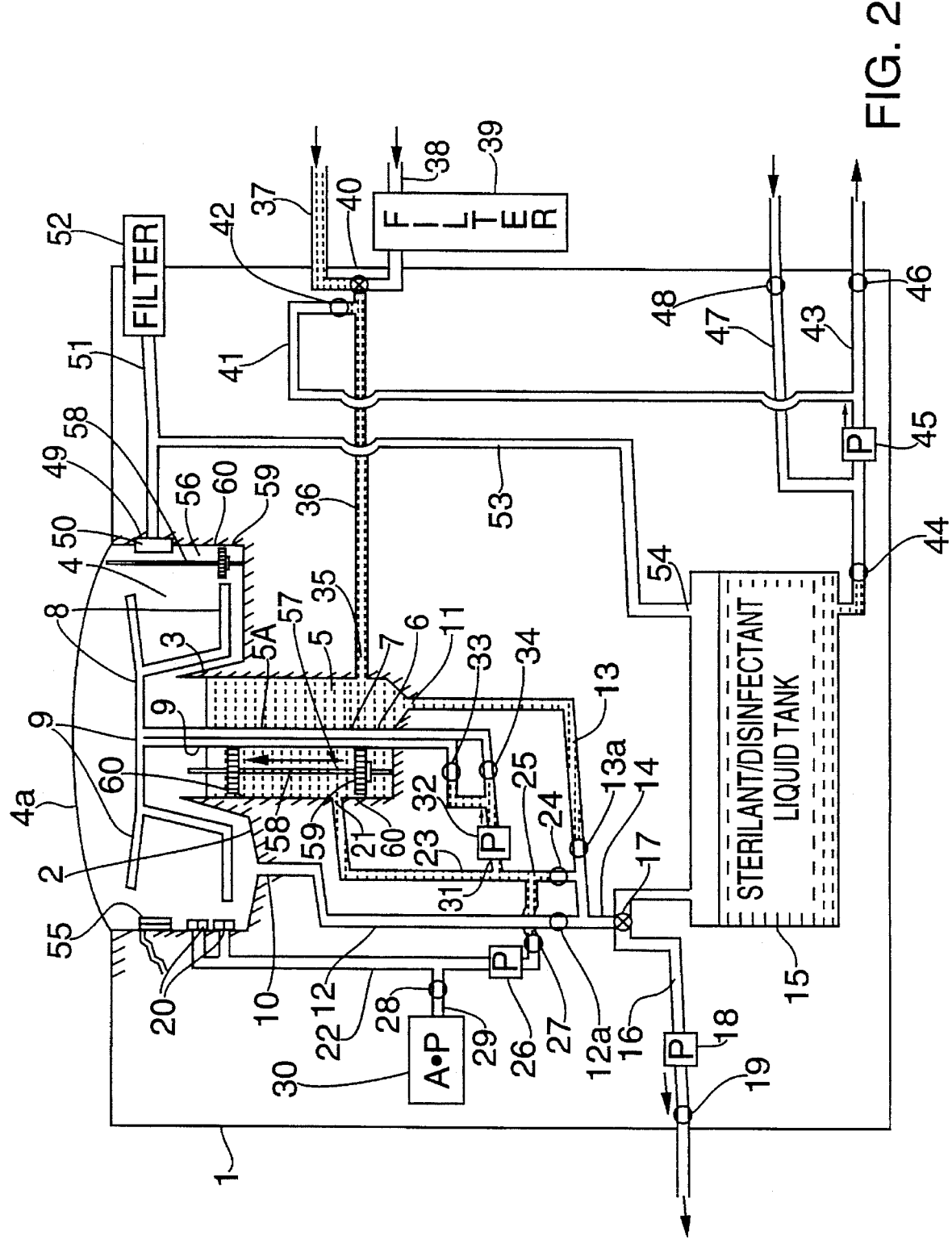
FIG. 2 is a schematic diagram illustrating the endoscope washer of FIG. 1 as it fills with tap water.

During this step, as shown in FIG. 2, the first, second, fourth, fifth, seventh, eighth, ninth, and tenth opening and closing valves 12a, 13a, 24, 27, 33, 34, 42, and 44 are closed, and the second switching valve 40 is switched to the side of the first water supplying tube 37. When tap water is supplied through the first water supplying tube 37, it is supplied from the fluid supplying port 35 through the water supplying pipe 36 to the washing fluid well 5 of the washing and disinfecting basin 2. At the same time, the second tube 23 and the second drain 13 are filled with the water.

Step Of Spraying Tap Water On Endoscope

Figure 3:
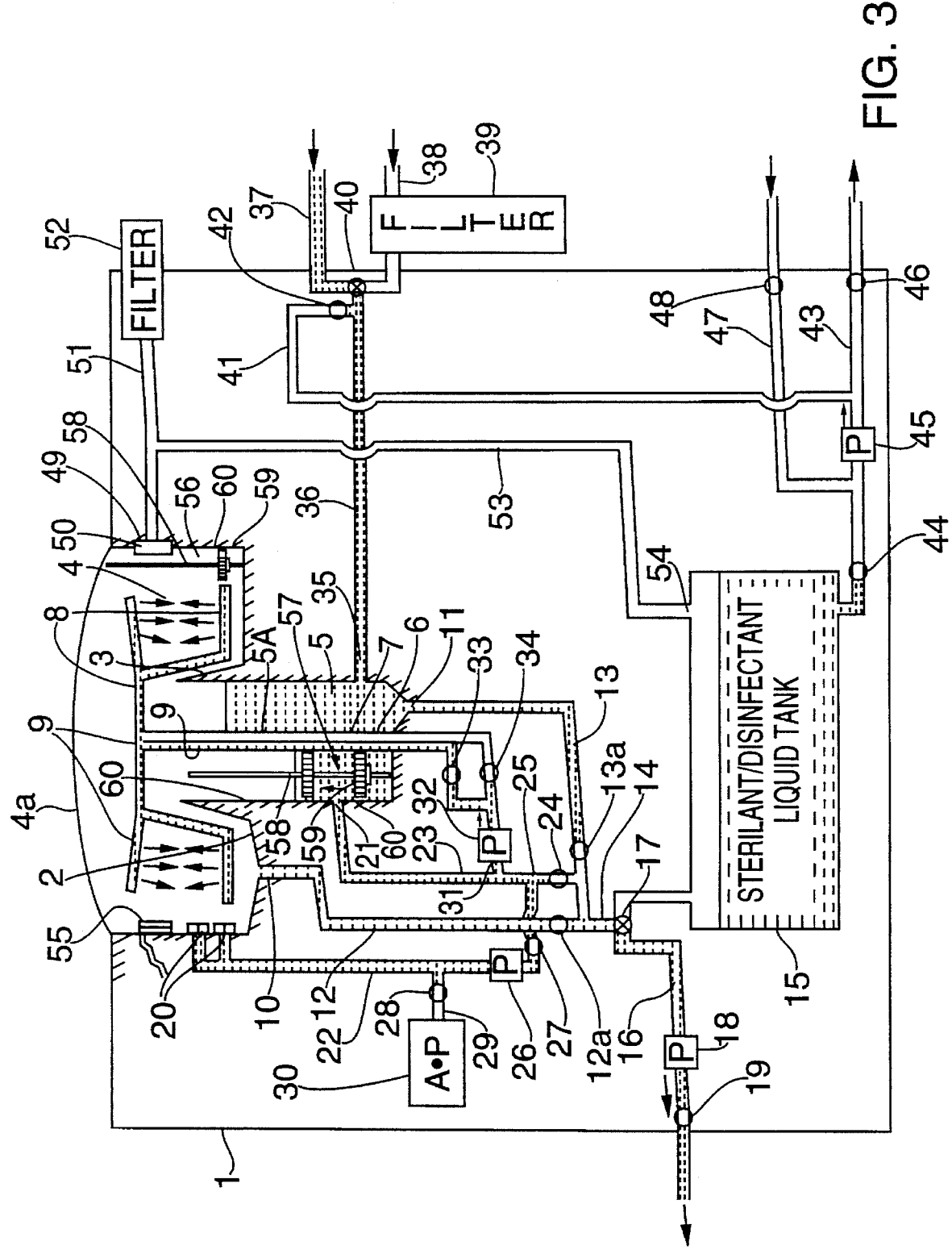
FIG. 3 is a schematic diagram illustrating the endoscope washer of FIG. 1 as it sprays tap water on an endoscope.

During this step, shown in FIG. 3, the second, fourth, sixth, eighty, ninth, and tenth opening and closing valves 13a, 24, 28, 34, 42, and 44 are closed, the first, third, fifth, and seventh opening and closing valves 12a, 19, 27, and 33 are opened, and the first switching valve 17 is switched to the side of the discharge pipe 16. When the first, second, and third pumps 18, 26, and 32 are activated, the tap water in the washing fluid well 5 is guided to the connector 20 through the first tube 22 by the second pump 26 and supplied to the channels of an endoscope, e.g., the air and water supplying channels and the forceps channel. At the same time, the tap water is guided into the fluid supplying branch pipes 8 through the first fluid supplying pipe 6, and sprayed on the outer surface of the endoscope through the nozzles 9. Thus, the internal lumens (channels) and the outer surface of the endoscope are washed.

The tap water supplied to the endoscope holding section 4, i.e., dirty water contaminated by the washing of the endoscope is discharged to the outside of the washer main body 1 by the first pump 18 through the first drain 12 and the discharge pipe 16. The above process continues, and when the level sensor 57 detects the decrease of the fluid in the washing fluid well 5, the second switching valve 40 periodically opens to resupply the tap water.

Step Of Draining Dirty Water

Figure 4:
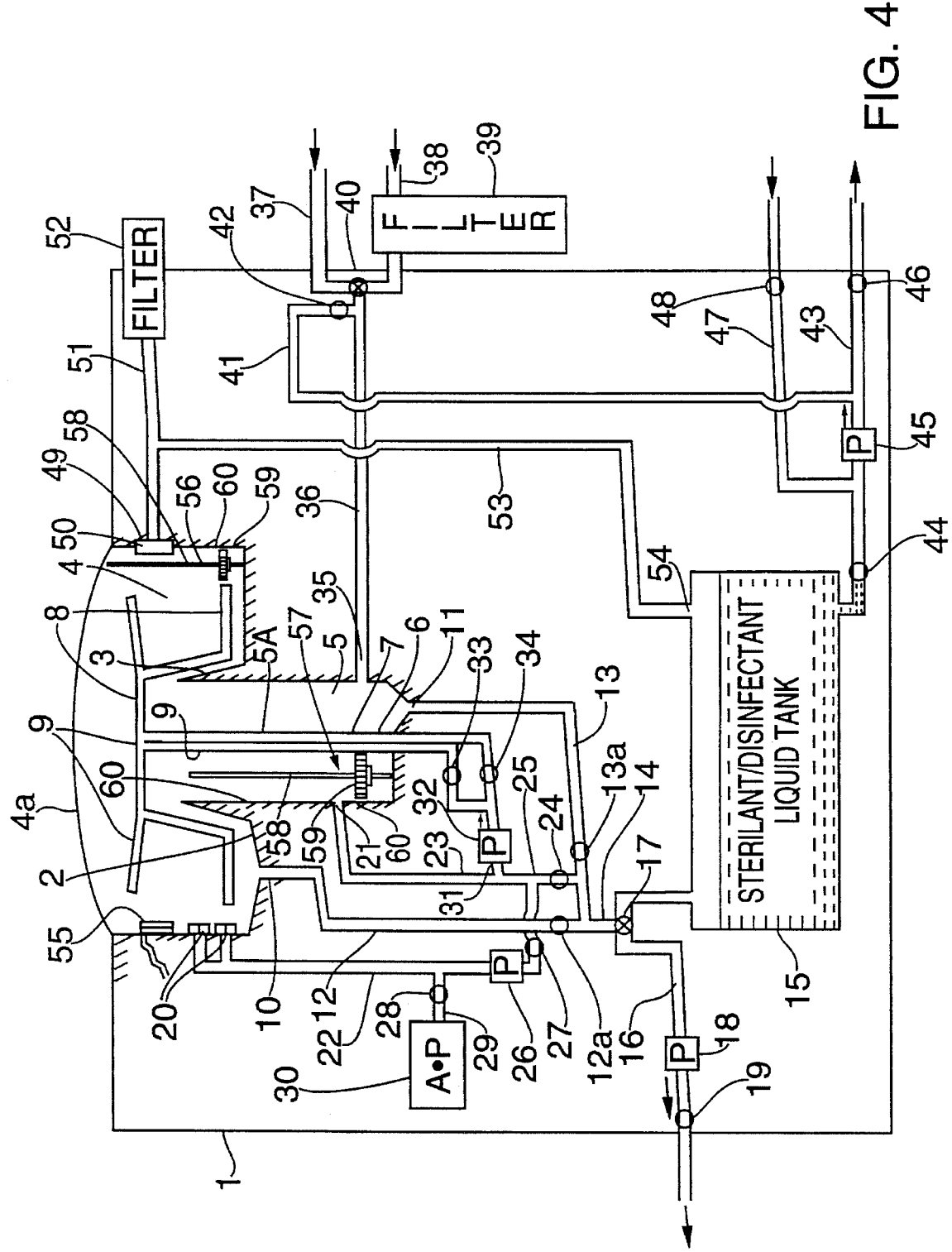
FIG. 4 is a schematic diagram illustrating the endoscope washer of FIG. 1 as dirty water drains from the endoscope washer.

As shown in FIG. 4, the second switching valve 40 is closed at the end of the spray wash step to stop the influx of the water. The first, second, third, fourth, sixth, seventh, and eighth opening and closing valves 12a, 13a, 19, 24, 28, 33, and 34 are opened, the first switching valve 17 is switched to the side of the discharge pipe 16.

The fourth opening and closing valve 27 is closed, and the air pump 30 is activated to supply air to the channels of the endoscope, e.g., the air and water supplying channels and the forceps channel, through the first tube 22 and the connector 20, thereby discharging the tap water. As a result, the tap water in the endoscope holding section 4, the washing fluid well 5, and the tubes are entirely discharged from the washer main body 1 through the discharge pipe 16.

Cleaning Step

Figure 5:
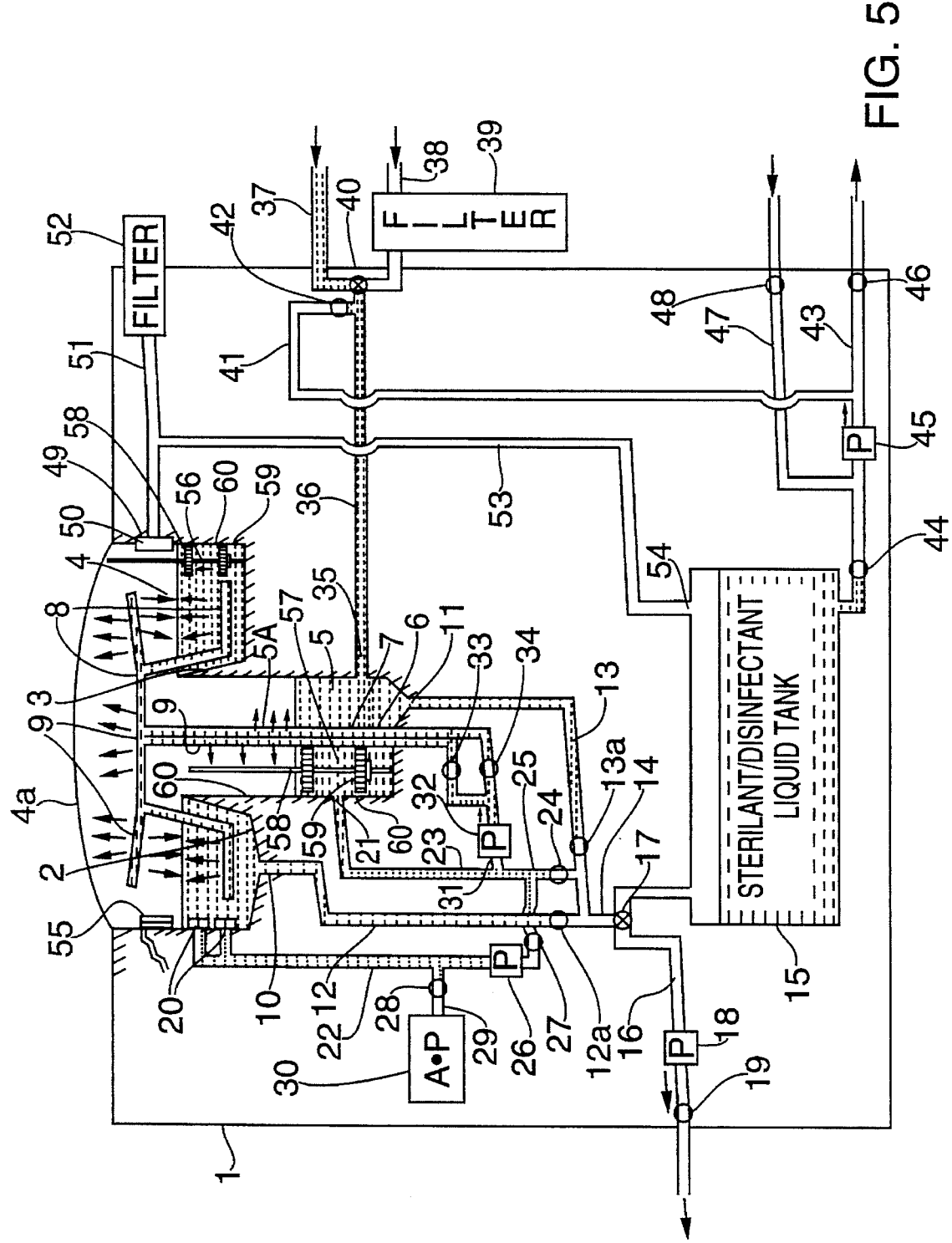
FIG. 5 is a schematic diagram illustrating the endoscope washer of FIG. 1 as it performs an endoscope cleaning step.

As shown in FIG. 5, the first, second, fourth, sixth, ninth, and tenth opening and closing valves 12a, 13a, 24, 28, 42, and 44 are closed, and the second switching valve 40 is switched to the side of the first water supplying tube 37. When tap water is supplied through the first water supplying tube 37, the tap water is supplied from the fluid supplying port 35 to the washing fluid well 5 of the washing and disinfecting basin 2 through the water supplying pipe 36.

When the second and third pumps 26 and 32 are activated, the tap water in the washing fluid well 5 is guided to the connector 20 by the second pump 26 through the first tube 22, and supplied to the channels of the endoscope, such as the air and water supplying channels and the forceps channel. At the same time, the tap water is guided to the fluid supplying branch pipes 8 through the first and second fluid supplying pipes 6 and 7 by the third pump 32, and sprayed on the interior of the washing fluid well and the outer surface of the endoscope in the endoscope holding section 4 through the nozzles 9.

When the endoscope holding section 4 is full of the tap water, the water spills over the partition 3 into the washing fluid well 5. When both the endoscope holding section 4 and the washing fluid well 5 are filled with a sufficient amount of the tap water, the second switching valve 40 closes off the tap water supply.

While the tap water is being supplied to the endoscope holding section 4 and the washing fluid well 5, detergent is added to the endoscope holding section 4 from the detergent box 55. The detergent water circulates through the endoscope holding section 4, the washing fluid well 5, the second tube 23, the first tube 22, and the connector 20, in this order, while circulating the outer surface and the channels of the endoscope, such as the air and water supplying channels and the forceps channel. At this time, ultrasonic transducers (not shown) attached to the bottom portion of the endoscope holding section 4 may be activated to ultrasonically clean the endoscope.

Step Of Draining Detergent Water

After cleaning, the detergent water in the washer main body 1 is completely drained in the same manner as in the step of draining dirty water illustrated in FIG. 4.

Step Of Rinsing With Clean water

To remove any detergent that remains in the endoscope washer, a rinsing step is performed using clean water. In the same manner as in the step of spraying tap water on the endoscope as shown in FIG. 3, clean water is supplied to the washer main body to rinse the detergent water from the portions of the endoscope and the washer main body. Thereafter, the eighth opening and closing valve 34 is opened again, the third pump 32 is activated, and the clean water is sprayed on the endoscope holding section 4 and the washing fluid well 5. Thereafter, the water in the washer main body 1 is completely discharged.

Step Of Sterilizing/Disinfecting Endoscope And Washer

Figure 6:
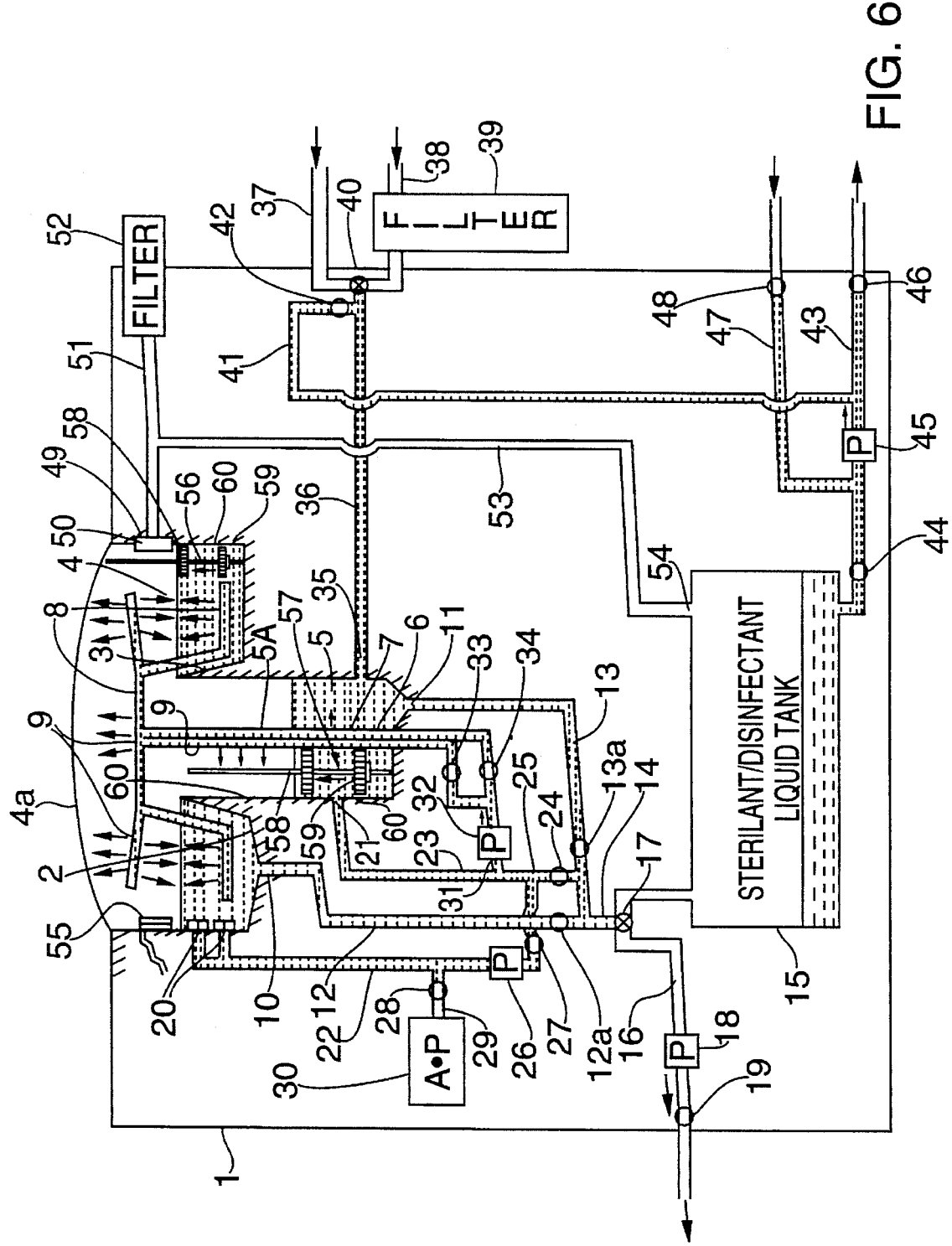
FIG. 6 is a schematic diagram illustrating the endoscope washer of FIG. 1 as it performs the step of sterilizing/disinfecting the endoscope and the endoscope washer.

During this step, as shown in FIG. 6, the first and second switching valves 17 and 40 are closed. The sixth, eleventh, and twelfth opening and closing valves 28, 46, and 48 are closed, and the second, third, fourth, fifth, seventh, eighth, ninth, and tenth opening and closing valves 13a, 19, 24, 27, 33, 34, 42, and 44 are opened.

When the second, third, and fourth pumps 26, 32, and 45 are activated, the sterilant/disinfectant in the sterilant/disinfectant tank 15 is supplied through the fourth tube 43, the third tube 41, and the water supplying pipe 36 to the washing fluid well 5 via the fluid supplying port 35. The sterilant/disinfectant in the washing fluid well 5 is guided from the second tube 23 by the second pump 26 to the connector 20 through the first tube 22, and supplied to the channels of the endoscope such as the air and water supplying channels and the forceps channel. At the same time, the sterilant/disinfectant is guided to the fluid supplying branch pipes 8 by the third pump 32 through the first and second fluid supplying pipes 6 and 7, and sprayed on the interior of the washing fluid well 5 and the outer surface of the endoscope in the endoscope holding section 4 through the nozzles 9.

When the endoscope holding section 4 is full of the sterilant/disinfectant and the endoscope is immersed therein, the sterilant/disinfectant spills over the partition 3 into the washing fluid well 5. When both the endoscope holding section 4 and the washing fluid well 5 are filled with a sufficient amount of the sterilant/disinfectant, the fourth pump 45 is stopped.

During the sterilization/disinfection cycle, the second, third, pumps 26 and 32, are continuously or periodically activated to keep all washer surfaces wet with the sterilant/ disinfectant. Moreover, the sterilant/disinfectant is brought into contact with the first and second switching valves 17 and 40 so that all the tubes in the washer main body can be sterilized/disinfected.

Optionally, the discharge pipe 16 between the first switching valve 17 and third opening and closing valve 19 may be filled with the sterilant/disinfectant. The part of sterilant/ disinfectant which fills this portion can be drained from the washer main body 1, if necessary, and the other part of sterilant/disinfectant can be collected in the sterilant/disinfectant tank 15 at the end of the cycle.

Note that in accordance with the present invention, the endoscope holding section 4 and the washing fluid well 5 are cleaned with detergent, and the entire washer is sterilized or disinfected with sterilant/disinfectant fluid at the same time the endoscope is processed. Accordingly, there is no need for a special washer self-disinfection cycle.

Step Of Draining Sterilant/Disinfectant

When the tenth opening and closing valve 44 is closed and the first switching valve 17 is opened so as to drain the sterilant/disinfectant fluid into the sterilant/disinfectant tank 15, the sterilant/disinfectant is collected by gravity in the sterilant/disinfectant tank 15. The sixth opening and closing valve 28 is opened and the air pump 30 is activated to force the sterilant/disinfectant from the channels of the endoscope such as the air and water supplying channels and the forceps channel.

Note that when sterilant/disinfectant is transferred either from the sterilant/disinfectant tank 15 to the endoscope holding section 4, or vice versa, the pressures in these fluid holding regions must be equal. However, since the air vent 54 of the sterilant/disinfectant tank 15 communicates with the vent 49 through the air branch tube 53 and the air tube 51, it is unnecessary to bring air in the washer or discharge air into the room through the charcoal filter 52. This design minimizes the exhaust of sterilant/disinfectant vapor into the room.

Step Of Rinsing With Sterile Water

Figure 7:
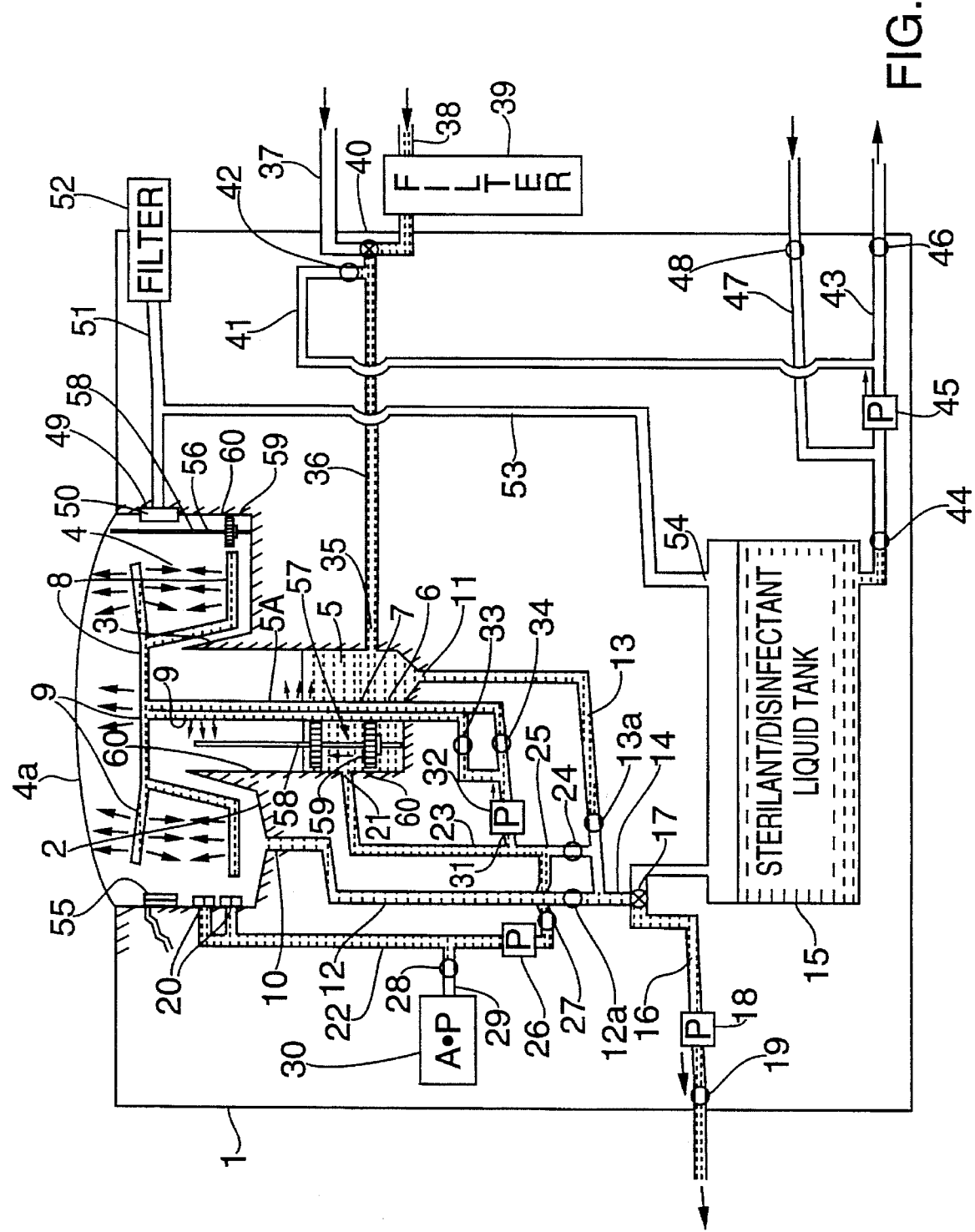
FIG. 7 is a schematic diagram illustrating the endoscope washer of FIG. 1 as it performs the step of rinsing the endoscope and endoscope washer with water.

Now that all internal tubes of the washer have been sterilized/disinfected, it is possible to bring sterile filtered water into the washer without recontaminating the endoscope or washer. As shown in FIG. 7, the second switching valve 40 is switched to the side of the second water supplying tube 38 to supply sterile water to the washing fluid well 5. Once the washing fluid well 5 is sufficiently filled, the second and third pumps 26 and 32 are activated to spray and thereby rinse the endoscope holding section 4 and the washing fluid well 5 with the sterile water, and to flush the sterile water through the channels of the endoscope such as the air and water supplying channels and the forceps channel.

The first and third opening and closing valves 12a and 19 are opened and the first pump 18 is activated, thereby draining the sterile water collects in the endoscope holding section 4. In this step, the sterilant/disinfectant is completely rinsed from the endoscope holding section 4 and the washing fluid well 5.

Step Of Draining

The sterile water in the washer and the channels of the endoscope are completely drained in the same manner as in the above described step of draining dirty water as shown in FIG. 4. At this time, the air pump 30 is activated to dry channels of the endoscope. The endoscope and washer sterilization/disinfection cycle is thus completed.

Step Of Sterilizing/Disinfecting The Washer During Periods Of Storage

Figure 8:
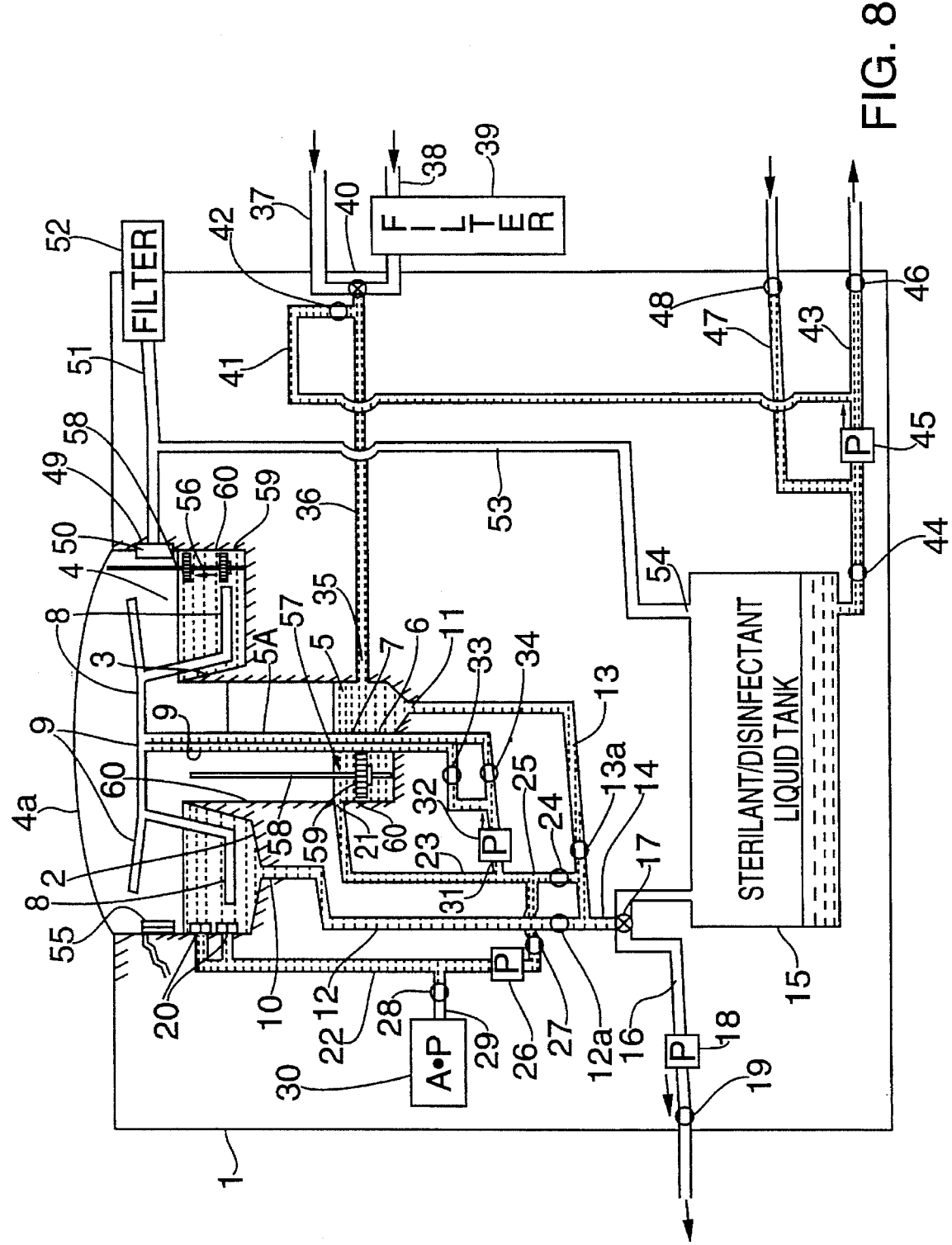
FIG. 8 is a schematic diagram illustrating the endoscope washer of FIG. 1 arranged for storage when the endoscope washer is to be kept idle, e.g., at night.

Referring now to FIG. 8, when the endoscope washer is idle, it can be stored with all internal tubes filled with sterilant/disinfectant as shown in FIG. 8. Sterilant/disinfectant can be sprayed periodically, e.g., once every hour, in the endoscope holding section and the washing fluid well 5 to prevent bacterial growth.

Figure 9:
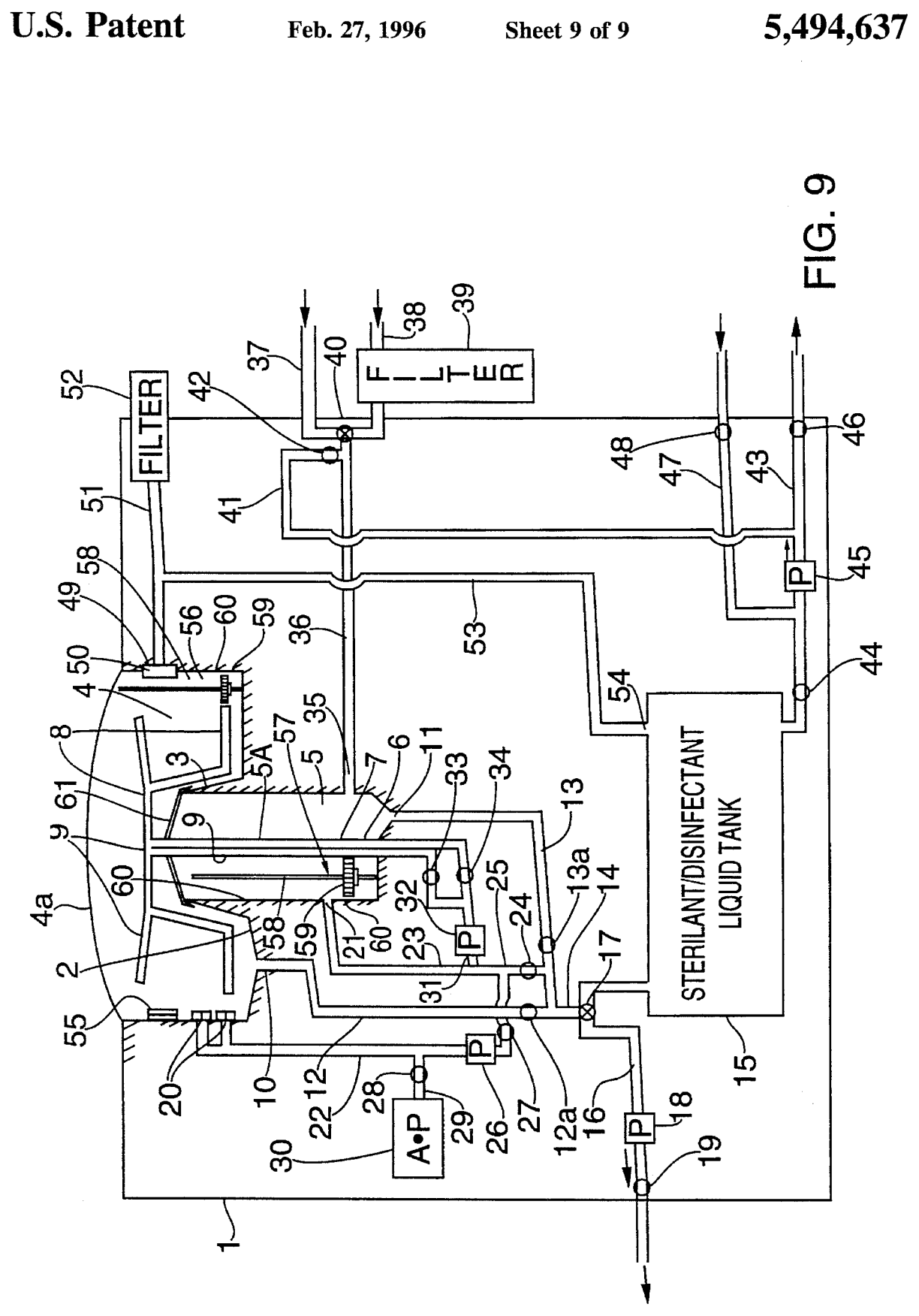

In accordance with another embodiment of the present invention, the washing fluid well 5 could be covered by a shield 61 as shown in FIG. 9, if the spraying of the endoscope holding section 4 should cause dirty water to enter the washing fluid well 5. If the shield 61 were provided, additional nozzles would have to be formed in the rotor 5A to clean and sterilize/disinfect the upper and lower surfaces of the shield. The use of the shield 61 has the additional advantage of preventing users from dropping objects or putting their hands into the well.

As described above, the present invention comprises a sterilant/disinfectant tank for supplying a sterilant/disinfectant fluid to an endoscope holding portion and a washing fluid well through the washing fluid tube, to provide a self-washing function for washing and sterilizing/disinfecting the endoscope and the washing fluid well simultaneously.

Therefore, the present invention is advantageous in that the washing basin and the fluid tubes can be self-sterilized/ disinfected automatically each time the endoscope is washed and sterilized/disinfected, not requiring special processes which the user must perform in order to sterilize/disinfect the washer. Furthermore, in accordance with the present invention unprocessed water, e.g., tap water, may be used for washing and processed water, e.g., sterile water, may be used for rinsing without decreasing performance, but with a decrease in operating costs as compared to the known systems which use only sterile water.

What is claimed is:

1. A disinfecting method comprising the steps of:

providing an endoscope re-processor including a washing fluid well, a basin for holding an endoscope to be reprocessed, a plurality of nozzles, and a tube for supplying a fluid to the plurality of nozzles;

providing an endoscope to be re-processed into the basin;

supplying a cleaning fluid through the tube to the plurality of nozzles;

spraying the cleaning fluid through the plurality of nozzles onto an interior wall of the basin and a surface of the endoscope, to wash the basin and the surface of the endoscope;

discharging the cleaning fluid from the washing fluid well and the basin after spraying the cleaning fluid;

supplying a disinfectant through the tube to the plurality of nozzles; and spraying the disinfectant through the plurality of nozzles onto the interior wall of the washing fluid well, the interior wall of the basin and the surface of the endoscope.

2. The method of claim 1, wherein the step of supplying a cleaning fluid through the tube to the plurality of nozzles includes the steps of:

collecting previously sprayed cleaning fluid in the washing fluid well; and pumping the previously sprayed cleaning fluid through the tube.

3. The method of claim 1, wherein the step of supplying a disinfectant through the tube to the plurality of nozzles includes the step of:

collecting previously sprayed disinfectant in the washing fluid well; and pumping the previously sprayed disinfectant through the tube.

4. The method of claim 3, further comprising the steps of:

discharging the disinfectant from the washing fluid well and the basin; and rinsing with water the endoscope, the washing fluid well and the basin to remove disinfectant residue therefrom.

5. The method o claim 4, further comprising the step of filtering the water prior to performing the rinsing step.

6. The method of claim 5, wherein the cleaning fluid is a detergent solution of water and detergent and wherein the step of filtering the water produces sterile water.

7. The method of claim 5, wherein the cleaning fluid is a detergent solution of non-processed water and detergent.

8. The method of claim 7, further comprising the steps of:

after discharging the cleaning fluid, spraying unprocessed water through the plurality of nozzles onto the outer surface of the endoscope and the interior wall of the basin to rinse any detergent residue; and draining the washing fluid well and the basin to discharge the unprocessed water.

9. The method of claim 8, further comprising the step of washing the endoscope with unprocessed water prior to washing with a cleaning solution by spraying the unprocessed water through the plurality of nozzles.

10. The method of claim 9, wherein the step of washing the endoscope with unprocessed water includes the steps of:

supplying unprocessed water to the washing fluid well;

supplying unprocessed water from the washing fluid well to the plurality of nozzles through a tube; and draining the washing fluid well and the basin to discharge the unprocessed water therefrom.

11. The method of claim 10, wherein the unprocessed water is tap water.

12. The method of claim 1, further comprising the steps of:

discharging the disinfectant from the washing fluid well and the basin; and spraying water through the plurality of nozzles onto the surface of the endoscope, the interior wall of the washing fluid well and the interior wall of the basin to rinse any disinfectant residue;

draining the washing fluid well and the basin to discharge the water.

13. An endoscope re-processor apparatus, comprising:

basin means for holding an endoscope;

fluid holding means coupled to the basin means for collecting reprocessing fluids;

spray means coupled to the fluid holding means for simultaneously spraying an endoscope to be reprocessed, the basin means and the fluid holding means with a reprocessing fluid.

14. The endoscope re-processor apparatus of claim 13, wherein the spray means is coupled to the fluid holding means by:

a tube used to supply the reprocessing fluids collected in the fluid holding means to the spray means.

15. The endoscope re-processor of claim 14 further comprising:

control means for controlling the supply and recirculation of reprocessing fluids, including a cleaning fluid, a disinfecting fluid and a rinsing fluid, through the spray means so that first the cleaning fluid, then the disinfecting fluid, followed by the rinsing fluid are supplied to the spray means and recirculated through the fluid holding means.

16. The endoscope re-processor of claim 15, wherein the fluid holding means is located below the basin means and includes a lidless top portion which opens onto the bottom of the basin means thereby permitting the reprocessing fluids to drain from the basin means into the fluid holding means.

17. An endoscope re-processor comprising:

a basin for holding an endoscope;

a topless fluid well for collecting reprocessing fluids which flow into the topless fluid well from the basin, the topless fluid well being coupled to the basin through an opening in the bottom of the basin through which the reprocessing fluid can flow;

spray nozzles located within the basin for spraying the endoscope and the interior of the basin; and a tube coupled to the topless fluid well and the spray nozzles for supplying the reprocessing fluids collected in the topless fluid well to the spray nozzles.

18. The endoscope re-processor of claim 17, further comprising a raised rim attached to the bottom of the basin and surrounding the opening in the bottom of the basin so that the reprocessing fluids flowing into the topless fluid well from the basin must pass over a top portion of the raised rim.

19. The endoscope re-processor of claim 17, further comprising: spray nozzles located within the topless fluid well for spraying the interior of the topless fluid well.

* * * * *